(12) United States Patent
Sendai

(10) Patent No.: US 11,369,329 B2
(45) Date of Patent: Jun. 28, 2022

(54) IMAGING SUPPORT APPARATUS, METHOD, AND PROGRAM FOR DETECTING AN ABNORMAL SITE IN A MEDICAL IMAGE

(71) Applicant: FUJIFILM CORPORATION, Tokyo (JP)

(72) Inventor: Tomonari Sendai, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 164 days.

(21) Appl. No.: 16/792,328

(22) Filed: Feb. 17, 2020

(65) Prior Publication Data
US 2020/0305821 A1 Oct. 1, 2020

(30) Foreign Application Priority Data
Mar. 27, 2019 (JP) .............................. JP2019-060365

(51) Int. Cl.
| | |
|---|---|
| *A61B 6/00* | (2006.01) |
| *G06T 7/00* | (2017.01) |
| *A61B 6/02* | (2006.01) |
| *A61B 6/04* | (2006.01) |

(52) U.S. Cl.
CPC .............. *A61B 6/502* (2013.01); *A61B 6/025* (2013.01); *A61B 6/0414* (2013.01);
(Continued)

(58) Field of Classification Search
CPC ......... A61B 6/025; A61B 6/04; A61B 6/0407; A61B 6/0414; A61B 6/0421;
(Continued)

(56) References Cited

U.S. PATENT DOCUMENTS

| | | | |
|---|---|---|---|
| 6,990,175 B2* | 1/2006 | Nakashima | A61B 6/032 378/92 |
| 8,139,712 B2* | 3/2012 | Kojima | A61B 6/502 378/37 |

(Continued)

FOREIGN PATENT DOCUMENTS

| | | |
|---|---|---|
| JP | 2001-187044 A | 7/2001 |
| JP | 2006-51198 A | 2/2006 |
| JP | 2012-020044 A | 2/2012 |

OTHER PUBLICATIONS

Extended European Search Report dated Sep. 7, 2020, issued in corresponding EP Patent Application No. 20159048.6.

*Primary Examiner* — Allen C. Ho
(74) *Attorney, Agent, or Firm* — Solaris Intellectual Property Group, PLLC

(57) ABSTRACT

An abnormal site detection unit detects an abnormal site included in a medical image acquired based on radiation transmitted through a subject. A position specifying unit generates positional information for specifying a position of the abnormal site based on a feature point of the subject included in the medical image in a case where the abnormal site is detected in the medical image. An information generation unit generates additional imaging instruction information, including information that indicates a type of additional imaging based on the abnormal site and information that indicates the position of the abnormal site based on the positional information, for instructing at least one additional imaging.

14 Claims, 13 Drawing Sheets

(52) U.S. Cl.
CPC .......... *A61B 6/0421* (2013.01); *A61B 6/4258* (2013.01); *A61B 6/4435* (2013.01); *A61B 6/4447* (2013.01); *A61B 6/4452* (2013.01); *A61B 6/486* (2013.01); *A61B 6/487* (2013.01); *A61B 6/488* (2013.01); *A61B 6/5211* (2013.01); *A61B 6/5217* (2013.01); *A61B 6/5247* (2013.01); *A61B 6/54* (2013.01); *A61B 6/542* (2013.01); *A61B 6/545* (2013.01); *G06T 7/0012* (2013.01); *G06T 2207/30068* (2013.01)

(58) Field of Classification Search
CPC ....... A61B 6/4233; A61B 6/4258; A61B 6/44; A61B 6/4429; A61B 6/4435; A61B 6/4447; A61B 6/4452; A61B 6/4458; A61B 6/4476; A61B 6/486; A61B 6/487; A61B 6/488; A61B 6/502; A61B 6/52; A61B 6/5205; A61B 6/5211; A61B 6/5217; A61B 6/5247; A61B 6/54; A61B 6/542; A61B 6/545
USPC ......... 378/22, 25, 26, 37, 62, 196, 197, 208, 378/209
See application file for complete search history.

(56) References Cited

U.S. PATENT DOCUMENTS

| | | | |
|---|---|---|---|
| 8,705,690 B2* | 4/2014 | Jerebko | G06T 19/00 378/21 |
| 9,642,581 B2* | 5/2017 | Lowe | A61B 6/4429 |
| 9,936,932 B2* | 4/2018 | Han | A61B 6/5241 |
| 10,448,911 B2* | 10/2019 | Erhard | A61B 6/4452 |
| 10,463,316 B2* | 11/2019 | Sugiyama | A61B 6/025 |
| 10,507,000 B2* | 12/2019 | Hoernig | A61B 6/463 |
| 10,531,849 B2* | 1/2020 | Shimada | A61B 6/4417 |
| 10,729,396 B2* | 8/2020 | Reicher | G16H 50/30 |
| 10,755,454 B2* | 8/2020 | Palma | G06T 5/00 |
| 10,776,919 B2* | 9/2020 | Kuratomi | G06T 5/003 |
| 10,789,712 B2* | 9/2020 | Yousef | G06V 10/255 |
| 10,796,430 B2* | 10/2020 | Bernard | A61B 8/5207 |
| 10,830,712 B2* | 11/2020 | Butani | A61B 6/42 |
| 10,888,291 B2* | 1/2021 | Shimada | A61B 6/0414 |
| 10,898,145 B2* | 1/2021 | Morita | A61B 6/469 |
| 10,945,694 B2* | 3/2021 | Choi | A61B 5/0035 |
| 10,993,689 B2* | 5/2021 | Palma | A61B 6/032 |
| 11,016,040 B2* | 5/2021 | Yamakawa | A61B 6/502 |
| 11,020,066 B2* | 6/2021 | Butani | A61B 6/4208 |
| 11,058,383 B2* | 7/2021 | Von Berg | A61B 6/5205 |
| 11,058,388 B2* | 7/2021 | Rempel | A61B 6/5247 |
| 11,069,060 B2* | 7/2021 | Kamei | G06T 7/0012 |
| 11,103,206 B2* | 8/2021 | Nakayama | A61B 6/482 |
| 11,127,137 B2* | 9/2021 | Heindl | A61B 6/032 |
| 11,129,594 B2* | 9/2021 | Sendai | A61B 6/502 |
| 11,154,257 B2* | 10/2021 | Morita | A61B 6/5205 |
| 11,246,551 B2* | 2/2022 | Butani | A61B 6/04 |
| 2006/0034503 A1 | 2/2006 | Shimayama | |
| 2006/0251301 A1 | 11/2006 | McNamara, Jr. et al. | |
| 2010/0067648 A1 | 3/2010 | Kojima | |

* cited by examiner

FIG. 6
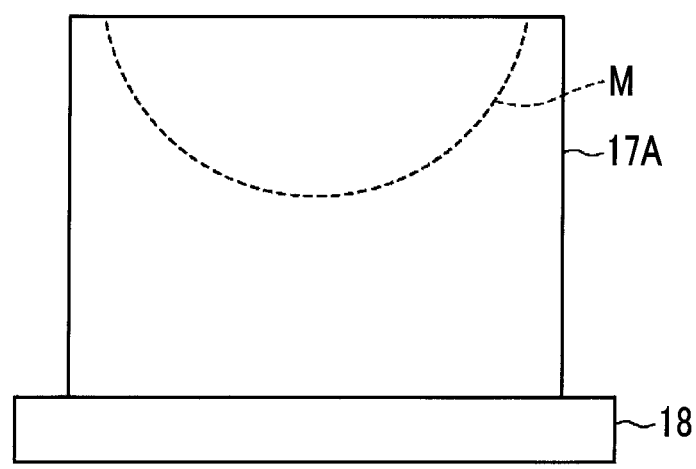
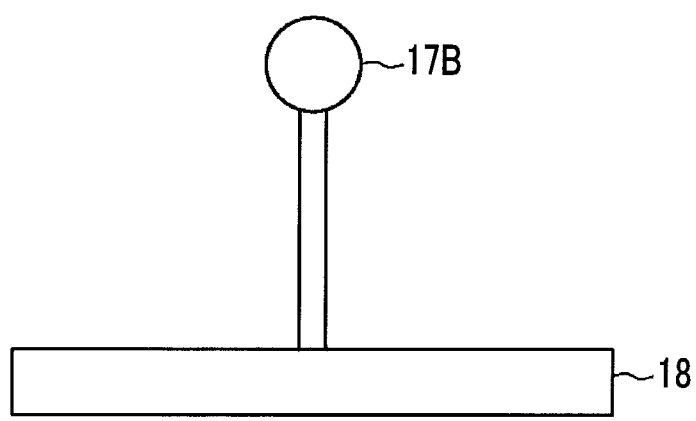
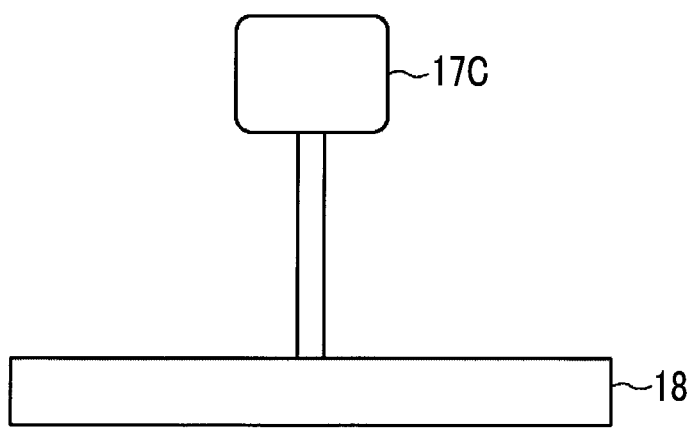

```
ABNORMAL SITE IS NOT INCLUDED IN
IMAGING AVAILABLE REGION.
PLEASE MOVE BREAST 5 cm TO LEFT.
```
~ 45

IMAGING SUPPORT APPARATUS, METHOD, AND PROGRAM FOR DETECTING AN ABNORMAL SITE IN A MEDICAL IMAGE

CROSS REFERENCE TO RELATED APPLICATIONS

The present application claims priority under 35 U.S.C. § 119 to Japanese Patent Application No. 2019-060365 filed on Mar. 27, 2019. The above application is hereby expressly incorporated by reference, in its entirety, into the present application.

BACKGROUND

Technical Field

The present disclosure relates to an imaging support apparatus, an imaging support method, and an imaging support program.

Related Art

In recent years, in order to promote early detection of breast cancer, image diagnosis using a radiographic imaging apparatus (called mammography) for imaging a breast has attracted attention. In mammography, a breast is placed on an imaging table and imaging is performed in a state where the breast is compressed by a compression plate. The breast mainly consists of mammary gland tissue and adipose tissue, and it is important for diagnosis to find a lesion such as a tumor and calcification hidden in the mammary gland tissue. Therefore, the radiation image of the breast (a breast image) imaged by mammography is used for the diagnosis by a doctor, after being image processed with a dedicated operation terminal or the like. The doctor examines the presence or absence of an abnormal site by displaying and interpreting the breast image on a display.

In a case where an abnormal site is found by the doctor, additional imaging is instructed by the doctor to perform more detailed examination. In this case, magnified imaging to magnify and image the position suspected of abnormality and to spot-magnified imaging to magnify and image only a position suspected of an abnormality are instructed. The radiological technician re-images the patient's breast according to the instructions from the doctor. The doctor makes a detailed diagnosis with respect to the abnormal site with reference to the breast image acquired by re-imaging.

On the other hand, in the medical field, a computer-aided diagnosis system (CAD, hereinafter referred to as CAD) that automatically detects an abnormal site such as a lesion in the image and highlights the detected abnormal site has been known. For example, the abnormal site such as calcification, a tumor, and spiculation is detected from the image of the breast using the CAD. Further, a method has been proposed in which the type of additional imaging is determined based on the detection result by the CAD, and the determined type of additional imaging is output (see, for example, JP2006-051198A and JP2001-187044A).

On the other hand, it takes time until the doctor interprets the breast image and determines whether there is an abnormality. Therefore, the patient needs to wait in the hospital until the doctor interprets the breast image, or go to the hospital again for examination. In order to reduce such a burden on the patient, it is conceivable that a radiological technician who performs imaging of the patient determines whether additional imaging is necessary by checking the acquired breast image. However, since the radiological technician is not a doctor, there are large variations in the interpretation determination results, and as a result, there is a tendency for variations in the determination of the necessity of re-imaging. Moreover, since the necessity of additional imaging is determined using the detection result by the CAD in the methods disclosed in JP2006-051198A and JP2001-187044A, there is a possibility of reducing a patient's burden. However, in the methods disclosed in JP2006-051198A and JP2001-187044A, although it can be recognized which type of additional imaging is to be performed by checking the output result of the type of additional imaging, it cannot be recognized which position on the breast is primarily imaged.

SUMMARY OF THE INVENTION

The present disclosure has been made in view of the aforementioned circumstances, the object thereof is to easily determine the necessity of additional imaging including a position to be additionally imaged.

An imaging support apparatus according to the present disclosure comprises an abnormal site detection unit that detects an abnormal site included in a medical image acquired based on radiation transmitted through a subject, a position specifying unit that generates positional information for specifying a position of the abnormal site based on a feature point of the subject included in the medical image in a case where the abnormal site is detected in the medical image, and an information generation unit that generates additional imaging instruction information, including information that indicates a type of additional imaging based on the abnormal site and information that indicates the position of the abnormal site based on the positional information, for instructing at least one additional imaging.

The imaging support apparatus according to the present disclosure may further comprise a determination unit that determines whether the position of the abnormal site is included in a prior image acquired by prior imaging before the additional imaging based on the positional information and the prior image in a case where the additional imaging is performed, and determines whether the position of the abnormal site is included in an imaging available region of the at least one additional imaging based on a result of the determination.

In the imaging support apparatus according to the present disclosure, in a case where the additional imaging instruction information is for instructing additional imaging of plural times, the determination unit may determine whether the position of the abnormal site is included in each imaging available region of the additional imaging of plural times.

In the imaging support apparatus according to the present disclosure, the prior image may be an optical image representing a surface of the subject, and may be a pre-image acquired by irradiating the subject with the radiation before the additional imaging.

The imaging support apparatus according to the present disclosure may further comprise a warning unit that issues a warning in a case where the position of the abnormal site is not included in the imaging available region of the at least one additional imaging.

The imaging support apparatus according to the present disclosure may further comprise a positioning information output unit that outputs positioning information for positioning the abnormal site in the imaging available region in a case where the position of the abnormal site is not included in the imaging available region of the at least one additional imaging.

The imaging support apparatus according to the present disclosure may further comprise a light source that emits light toward the subject, a light source driving unit that drives the light source so that the position of the abnormal site in the surface of the subject is irradiated with light emitted from the light source, and a light source control unit that controls driving of the light source driving unit based on the result of the determination by the determination unit.

In the imaging support apparatus according to the present disclosure, the subject may be a breast.

In the imaging support apparatus according to the present disclosure, the position specifying unit may generate the positional information for specifying the position of the abnormal site by detecting a nipple position of the breast and at least two positions on at least one of a skin line or a chest wall as the feature point.

In the imaging support apparatus according to the present disclosure, the information generation unit may generate the additional imaging instruction information including compression plate information indicating a type of a compression plate that compresses the breast.

The imaging support apparatus according to the present disclosure may further comprise a compression plate warning unit that issues a warning in a case where a compression plate used for the additional imaging is different from the compression plate indicated by the compression plate information.

An imaging support method according to the present disclosure comprises detecting an abnormal site included in a medical image acquired based on radiation transmitted through a subject, generating positional information for specifying a position of the abnormal site based on a feature point of the subject included in the medical image in a case where the abnormal site is detected in the medical image, and generating additional imaging instruction information, including information that indicates a type of additional imaging based on the abnormal site and information that indicates the position of the abnormal site based on the positional information, for instructing at least one additional imaging.

The imaging support method according to the present disclosure may be provided as a program for which a computer is caused to perform.

Another imaging support apparatus according to the present disclosure comprises a memory that stores a command to be executed by a computer, and a processor configured to execute the stored commands. The processor executes a step of detecting an abnormal site included in a medical image acquired based on radiation transmitted through a subject, a step of generating positional information for specifying a position of the abnormal site based on a feature point of the subject included in the medical image in a case where the abnormal site is detected in the medical image, and a step of generating additional imaging instruction information, including information that indicates a type of additional imaging based on the abnormal site and information that indicates the position of the abnormal site based on the positional information, for instructing at least one additional imaging.

According to the present disclosure, it is possible to easily determine necessity of additional imaging including a position to be additionally imaged.

BRIEF DESCRIPTION OF THE DRAWINGS

FIG. 6 is a diagram for explaining a type of compression plate.

DETAILED DESCRIPTION

Figure 1:
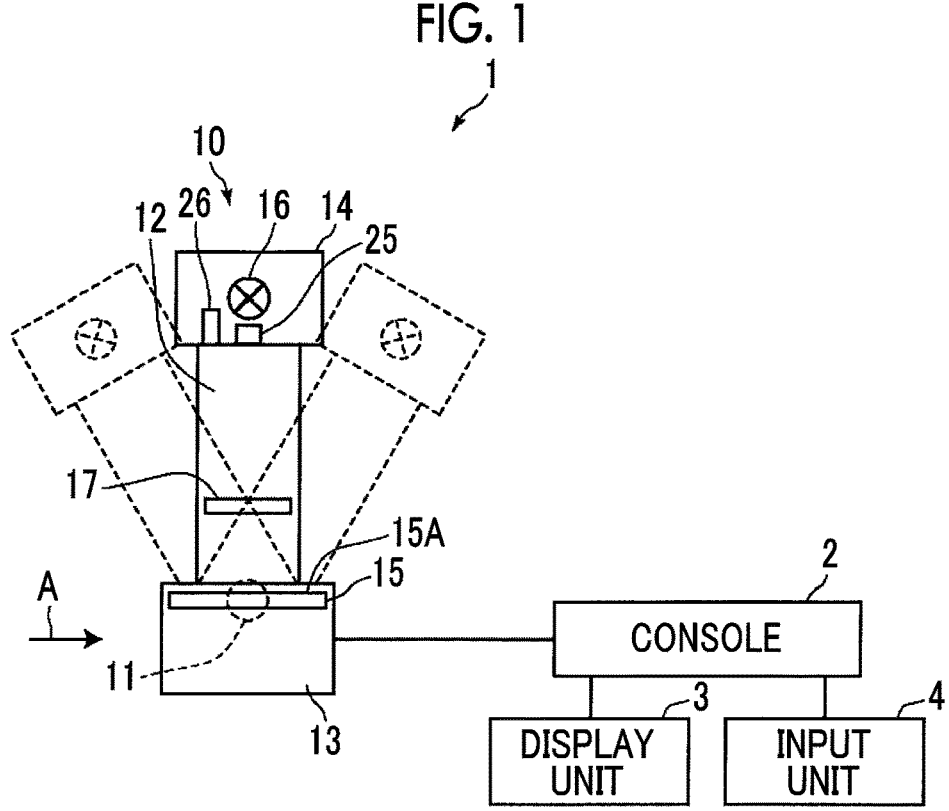
FIG. 1 is a schematic configuration diagram of a radiation image capturing system to which an imaging support apparatus according to the embodiment of the present disclosure is applied.
Figure 2:
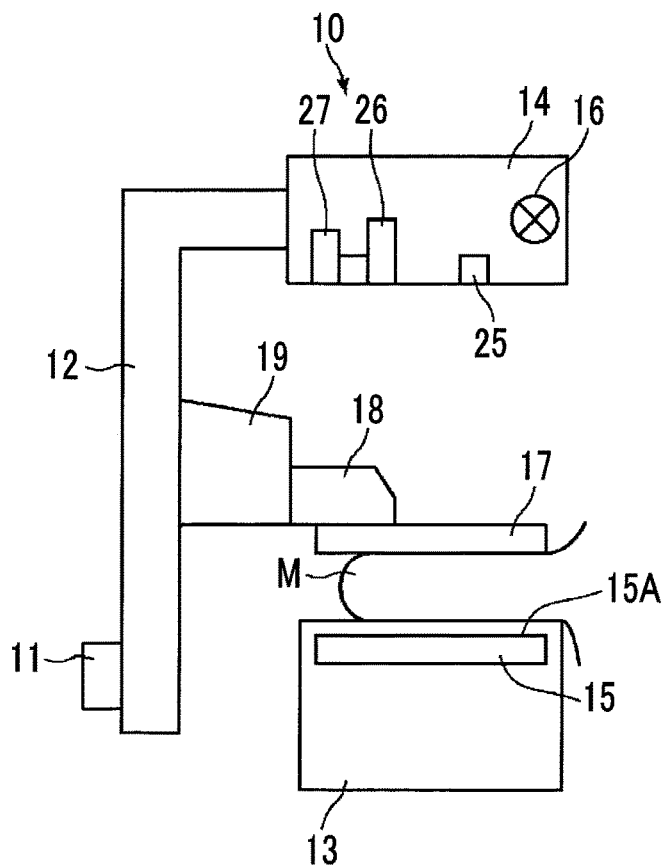
FIG. 2 is a diagram of a mammography apparatus viewed from a direction of arrow A in FIG. 1.

Hereinafter, the embodiments of the present disclosure will be described with reference to the diagrams. FIG. 1 is a schematic configuration diagram of a radiation image capturing system to which an imaging support apparatus according to the embodiment of the present disclosure is applied, and FIG. 2 is a diagram of a mammography apparatus included in the radiation image capturing system viewed from a direction of arrow A in FIG. 1.

As shown in FIG. 1, the radiation image capturing system 1 of the present embodiment comprises a console 2 and a mammography apparatus 10. The console 2 comprises a display unit 3 and an input unit 4.

The radiation image capturing system 1 of the present embodiment has a function of imaging a breast to acquire a breast image which is a radiation image of a breast by the mammography apparatus 10 operated by an operator such as a doctor or a radiological technician based on instructions (imaging orders) input from an external system (for example, a radiology information system (RIS)) via the console 2. In the present embodiment, the mammography apparatus 10 can generate both a tomographic image of a breast and a two-dimensional breast image by performing both tomosynthesis imaging and simple imaging in various imaging directions. The two-dimensional breast image means a breast image obtained by simple imaging.

The mammography apparatus 10 comprises an arm unit 12 connected to a base (not shown) by a rotary shaft 11. An imaging table 13 is attached to one end portion of the arm unit 12, and a radiation emission unit 14 is attached to the other end portion so as to face the imaging table 13. The arm unit 12 is configured so that only the end portion to which the radiation emission unit 14 is attached can rotate. Therefore, it is possible to rotate only the radiation emission unit 14 with the imaging table 13 fixed. The rotation of the arm unit 12 is controlled by the console 2.

The imaging table 13 comprises a radiation detector 15 such as a flat panel detector therein. The radiation detector 15 has a detection surface 15A of radiation. In addition, a circuit board on which a charge amplifier for converting a charge signal read from the radiation detector 15 into a voltage signal, a sampling two correlation pile circuit for sampling the voltage signal output from the charge amplifier, an analog digital (AD) conversion unit for converting the voltage signal into a digital signal, and the like are provided is provided inside the imaging table 13. Although the radiation detector 15 is used in the present embodiment, the detection unit is not limited to the radiation detector 15 as long as radiation can be detected and converted into an image.

The radiation detector 15 can perform recording and reading of a radiation image repeatedly, and may use a so-called direct-type radiation detector that directly converts radiation, such as X-rays, into electric charges, or a so-called indirect-type radiation detector that converts radiation into visible light and then converts the visible light into a charge signal. As a method of reading a radiation image signal, it is desirable to use a so-called thin film transistor (TFT) reading method in which a radiation image signal is read by ON and OFF of a TFT switch, or a so-called optical reading method in which a radiation image signal is read by emission of reading light, however, other methods may also be used without being limited to the above methods.

A radiation source 16 is accommodated in the radiation emission unit 14. The radiation source 16 emits X-rays as radiation and the timing of emission of radiation from the radiation source 16, and a radiation generation condition in the radiation source 16, that is, selection of target and filter materials, a tube voltage, an emission time, and the like are controlled by the console 2. In addition, a camera 25 for capturing an optical image of a breast M positioned on the imaging table 13 is provided inside the radiation emission unit 14. The camera 25 is provided in the radiation emission unit 14 so as not to be positioned on the optical path of the radiation emitted from the radiation source 16. The camera 25 may be movable on the radiation optical path as necessary. The radiation emission unit 14 is provided with a spot light source 26 that irradiates the breast M with spot light.

The direction of the spot light emitted from the spot light source 26 is controlled by the light source driving unit 27 as described below.

The arm unit 12 includes compression plate 17 that compresses the breast M, a support unit 18 that supports the compression plate 17, and a moving mechanism 19 that moves the support unit 18 in the vertical direction in FIGS. 1 and 2. Information on the distance between the compression plate 17 and the imaging table 13, that is, a compression thickness is input to the console 2. The compression plate 17 is prepared in a plurality of sizes and shapes according to the type of imaging. Therefore, the compression plate 17 is attached to the support unit 18 in a replaceable manner.

The display unit 3 is a display device such as a cathode ray tube (CRT) or a liquid crystal monitor, and displays a message required for the operation, and the like in addition to a breast image as described below. The display unit 3 may include a speaker that outputs sound.

The input unit 4 includes an input device such as a keyboard, a mouse, or a touch panel, and receives an operation of the mammography apparatus 10 by the operator. The input unit 4 also receives an input of various kinds of information such as imaging conditions and instructions of correction of the information, which are required to perform the imaging. In the present embodiment, each unit of the mammography apparatus 10 operates according to the information from the input unit 4 input by the operator.

An imaging support program according to the present embodiment is installed in the console 2. In the present embodiment, the console 2 may be a workstation or a personal computer that is directly operated by the operator, or may be a server computer connected to these through a network. The imaging support program is distributed in a state of being recorded on a recording medium such as a digital versatile disc (DVD) or a compact disc read-only memory (CD-ROM), and is installed in the computer from the recording medium. Alternatively, the imaging support program is stored in a storage device of a server computer connected to the network, or in a network storage so as to be accessible from the outside, and is downloaded and installed in the computer as necessary.

Figure 3:
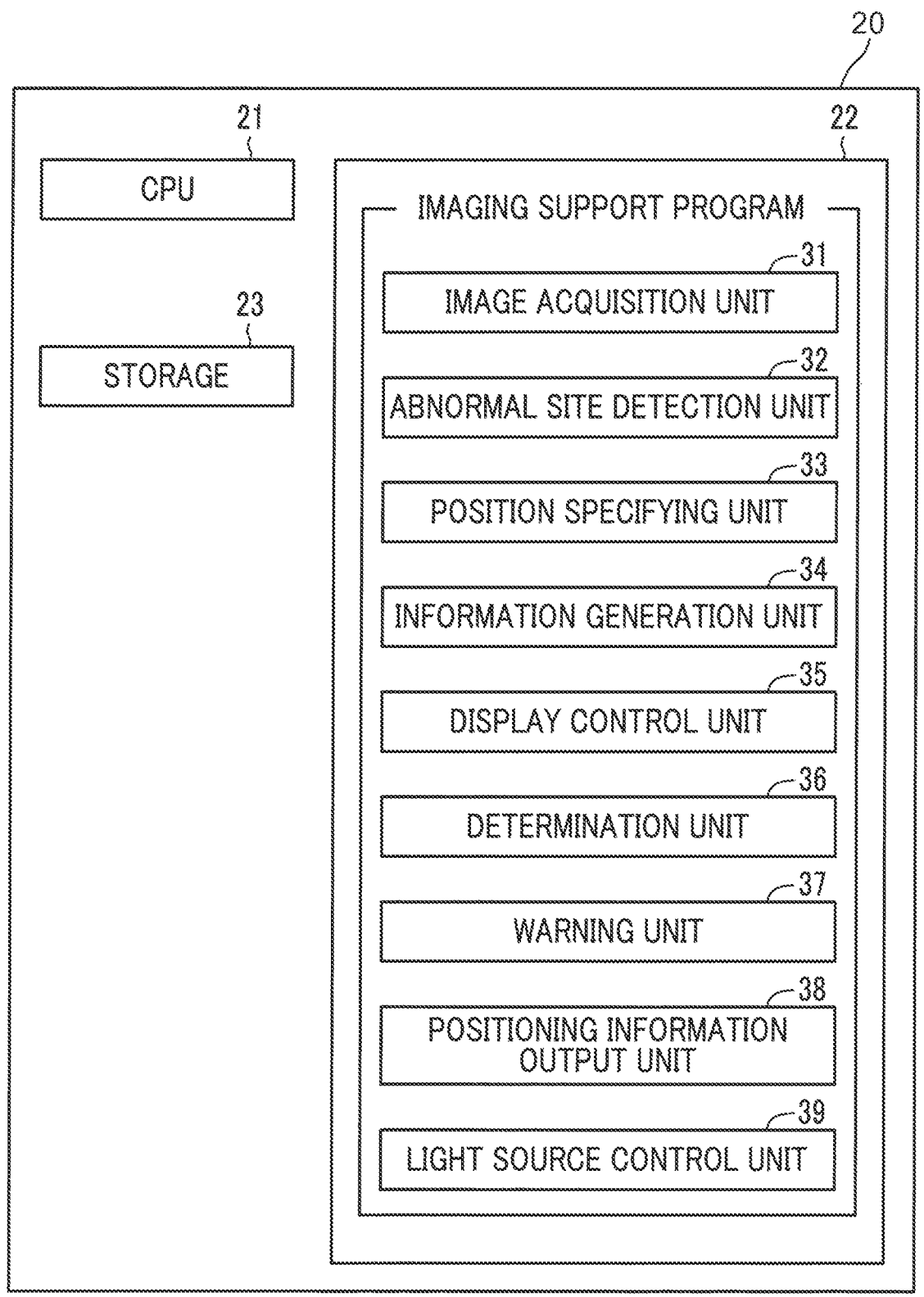
FIG. 3 is a diagram showing the schematic configuration of the imaging support apparatus realized by installing an imaging support program in a computer constituting a console in the present embodiment.

FIG. 3 is a diagram showing the schematic configuration of the imaging support apparatus to be realized by installing an imaging support program according to the present embodiment in a computer constituting the console 2 in the present embodiment. As shown in FIG. 3, the imaging support apparatus 20 comprises a central processing unit (CPU) 21, a memory 22, and a storage 23 as the configuration of a standard computer.

The storage 23 includes a storage device such as a hard disk drive or a solid state drive (SSD), and stores various kinds of information including a program for driving each unit of the mammography apparatus 10 and the imaging support program. In addition, a breast image acquired by imaging is also stored in the storage 23.

The memory 22 temporarily stores programs and the like stored in the storage 23 so that the CPU 21 executes various kinds of processing. The imaging support program causes the CPU 21 to execute: image acquiring processing of acquiring the breast image by causing the mammography apparatus 10 to image a breast; abnormal site detection processing of detecting the abnormal site included in the breast image; position specifying processing of generating positional information for specifying the position of the abnormal site based on the feature point of the breast included in the breast image in a case where the abnormal site is detected in the breast image; information generation processing of generating additional imaging instruction information, including information that indicates a type of additional imaging based on the abnormal site and information that indicates the position of the abnormal site based on the positional information, for instructing at least one additional imaging; display control processing of displaying the additional imaging instruction information on the display unit 3; determination processing of determining whether the position of the abnormal site is included in a prior image acquired by prior imaging before the additional imaging based on the positional information and the prior image in a case where the additional imaging is performed, and determining whether the position of the abnormal site is included in the imaging available region of additional imaging based on the result of the determination; warning processing of issuing a warning in a case where the position of the abnormal site is not included in an imaging available region of additional imaging; positioning information output processing of outputting positioning information for positioning the abnormal site in the imaging available region in a case where the position of the abnormal site is not included in the imaging available region of additional imaging; and light source control processing of controlling the light source driving unit 27 described below.

In a case where the CPU 21 executes these kinds of processing according to the imaging support program, the CPU 21 of the console 2 functions as the image acquisition unit 31, the abnormal site detection unit 32, the position specifying unit 33, the information generation unit 34, the display control unit 35, and the determination unit 36, a warning unit 37, a positioning information output unit 38, and a light source control unit 39.

In a case of performing the image acquiring processing, the image acquisition unit 31 drives the mammography apparatus 10 based on instructions from the input unit 4 and performs imaging of the breast M by the instructed imaging method to acquire a breast image. For example, in the present embodiment, the image acquisition unit 31 performs imaging from two directions of cranio-caudal (CC) and medio-lateral oblique (MLO) with respect to one breast to acquire two breast images. Therefore, the image acquisition unit 31 acquires four breast images by combining the right and left breasts M. For each of the right and left breasts M, imaging from either the CC or MLO direction may be performed to obtain two breast images.

Figure 4:
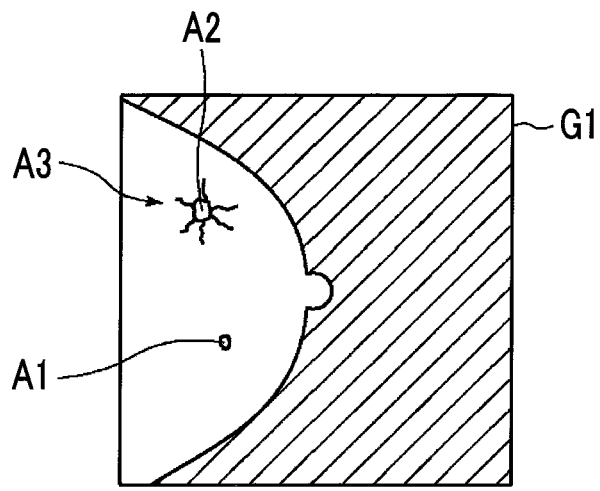
FIG. 4 is a diagram for explaining detection of an abnormal site.

The abnormal site detection unit 32 detects the abnormal site from the breast image. In the present embodiment, a site suspected of being abnormal such as calcification, a tumor, and spiculation included in the breast M is detected as the abnormal site. FIG. 4 is a diagram for explaining detection of the abnormal site. As shown in FIG. 4, the abnormal site detection unit 32 detects, from a breast image G1, an abnormal site A1 of calcification, an abnormal site A2 of a tumor, an abnormal site A3 of spiculation, and the like.

The abnormal site detection unit 32 detects abnormal sites A1 to A3 from the breast image G1 using a known computer-aided diagnosis (CAD, hereinafter referred to as CAD) algorithm. As a detection method using the CAD, for example, a morphological operation described in JP2008-016283A can be used. Also, a method described in JP2018-097463A may be used that detects the abnormal site using a learned model which is machine-learned so that the abnormal site can be detected. The detection method of the abnormal site by the abnormal site detection unit 32 is not limited to these methods, and any method can be used.

In the present embodiment, the abnormal site detection unit 32 detects the position of the abnormal site, the type of the abnormal site, the size of the abnormal site, and the like, and outputs the above information to the position specifying unit 33, the information generation unit 34, and the like as abnormal site information. The position of the abnormal site is a coordinate value of the abnormal site in the breast image G1. More specifically, for example, the coordinate value of the centroid position of the abnormal site. The size of the abnormal site is an area obtained by multiplying the number of pixels of the abnormal site included in the region of the abnormal site or the number of pixels of the abnormal site by the area per pixel of the breast image G1.

Figure 5:
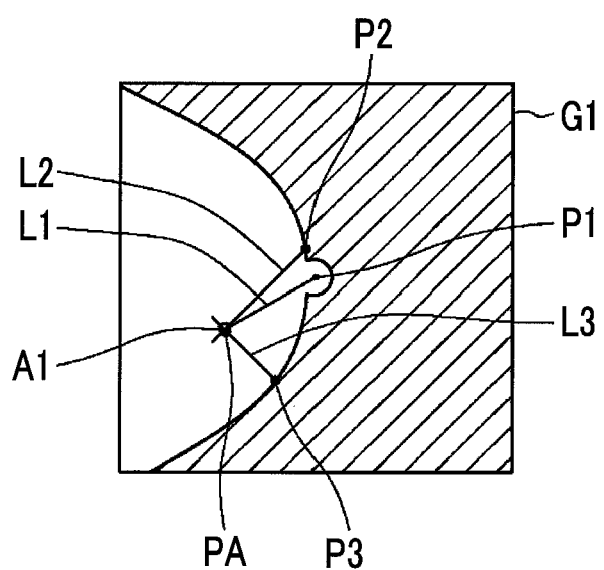
FIG. 5 is a diagram for explaining the generation of positional information.

A position specifying unit 33 generates positional information for specifying the position of the abnormal site based on the feature point of the breast M included in the breast image G1 in a case where the abnormal site is detected in the breast image G1. Specifically, the position specifying unit 33 generates positional information based on one or more, preferably at least three feature points. In the present embodiment, one feature point is specified at the nipple position included in the breast image G1, and two feature points are specified at the position of the skin line. The position specifying unit 33 generates the positional information for specifying the position of the abnormal site using the specified three feature points. FIG. 5 is a diagram for explaining the generation of the positional information. In FIG. 5, for the sake of explanation, it is assumed that only one abnormal site A1 is specified in the breast image G1. On the two-dimensional plane, in a case where three points and the distance from the three points are specified, one position can be specified. For this purpose, in the present embodiment, the position specifying unit 33 firstly specifies three feature points.

The abnormal site A1 has a certain area. Therefore, the position specifying unit 33 specifies the centroid position of the abnormal site A1 as a position PA of the abnormal site A1. The position specifying unit 33 specifies the nipple position as one of the feature points. For this purpose, the position specifying unit 33 extracts the nipple from the breast image G1. As a method for extracting the nipple, a learned model which is learned by machine learning so that the nipple can be detected may be used, or a method for specifying the nipple using a template may be used. In a case where the position specifying unit 33 specifies the nipple, the centroid position of the nipple is obtained, and the centroid position of the nipple is specified as a feature point P1.

The position specifying unit 33 specifies the positions on the skin line where the distance from the position PA of the abnormal site A1 is the shortest as feature points P2 and P3. The feature points P2 and P3 are on positions in the upper skin line and the lower skin line with respect to the nipple in the breast image G1. Furthermore, the position specifying unit 33 derives a distance L1 between the feature point P1 and the position PA of the abnormal site A1, a distance L2 between the feature point P2 and the position PA of the abnormal site A1, and a distance L3 between the feature point P3 and the position PA of the abnormal site A1. The position specifying unit 33 outputs the positions of the three feature points P1 to P3 and the distances L1 to L3 to the information generation unit 34 and the light source control unit 39 as the positional information for specifying the position of the abnormal site.

An information generation unit 34 generates additional imaging instruction information, including information that indicates a type of additional imaging based on the abnormal site and information that indicates the position of the abnormal site, for performing at least one additional imaging. In the present embodiment, additional imaging instruction information for performing one additional imaging is generated. For this purpose, the information generation unit 34 specifies the type of abnormal site detected by the abnormal site detection unit 32. For the type of abnormal site, the abnormal site information output by the abnormal site detection unit 32 need only be referred to. The information indicating the position of the abnormal site is derived from the positional information generated by the position specifying unit 33.

The information generation unit 34 specifies the type of additional imaging according to the type of the abnormal site. In the present embodiment, a table in which the type of the abnormal site is associated with the type of additional imaging is stored in the storage 23. The information generation unit 34 specifies the type of additional imaging according to the type of the abnormal site with reference to the table stored in the storage 23. Specifically, in a case where the abnormal site is calcification, magnified imaging or spot-magnified imaging is specified as the type of the additional imaging. Also, in a case where the abnormal site is a tumor or spiculation, spot imaging is specified as the type of additional imaging. In a case where the type of the abnormal site is input, a learned model that is learned to output the type of additional imaging according to the type of the abnormal site may be provided in the information generation unit 34, and the type of additional imaging according to the type of the abnormal site may be specified by the learned model.

On the other hand, as described above, the compression plate 17 is prepared in a plurality of sizes and shapes according to the type of imaging, and is attached to the support unit 18 in a replaceable manner. FIG. 6 is a plan view of various compression plates for explaining the type of compression plate. As shown in FIG. 6, as the type of the compression plate 17, a compression plate 17A capable of compressing the whole breast M, a small size compression plate 17B for spot imaging, and a medium size compression plate 17C for spot imaging are prepared.

Therefore, the information generation unit 34 specifies the type of the compression plate 17 according to the size of the abnormal site included in the abnormal site information, and generates additional imaging instruction information including information on the type of the compression plate 17. In the present embodiment, the table in which the size of the abnormal site is associated with the type of the compression plate 17 is stored in the storage 23. The information generation unit 34 acquires information on the type of the compression plate 17 according to the size of the abnormal site with reference to the table. In a case where the size of the abnormal site is input, a learned model that is learned to output the size of the compression plate 17 according to the type of the abnormal site may be provided in the information generation unit 34, and the size of the compression plate 17 according to the type of the abnormal site may be specified by the learned model.

The information generation unit 34 generates a specific image representing the position of the abnormal site by adding a mark to the position of the abnormal site in the breast image G1 using the positional information of the abnormal site generated by the position specifying unit 33. The specific image is included in the additional imaging instruction information.

Figure 7:
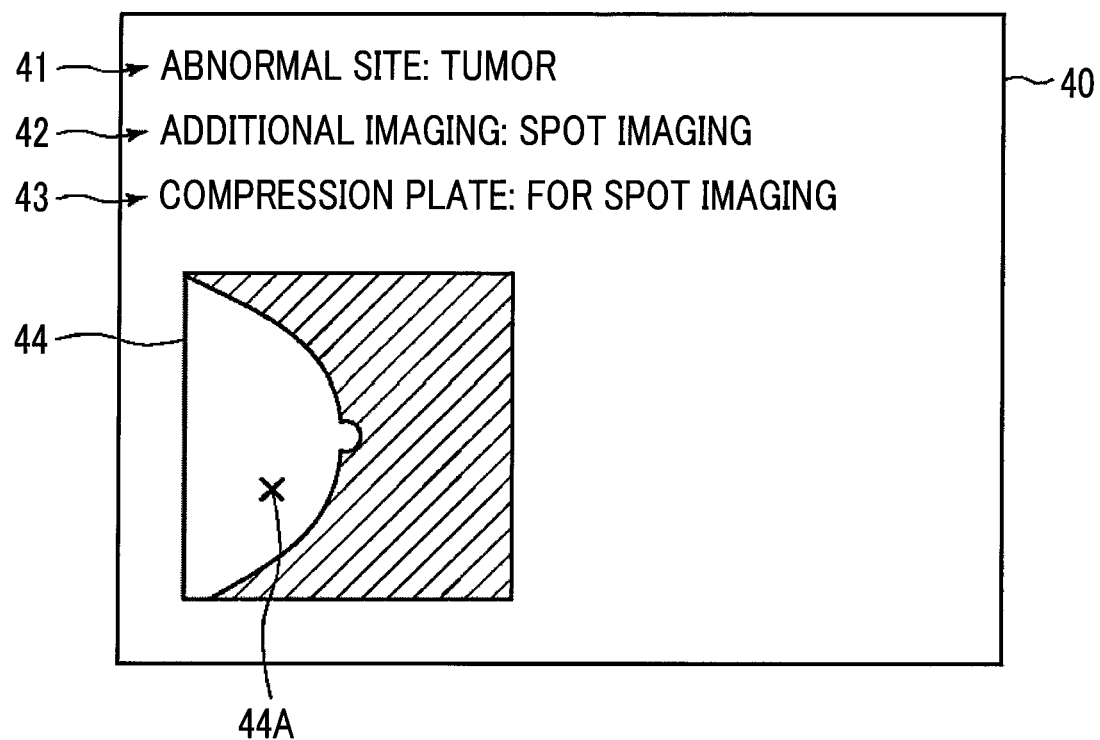
FIG. 7 is a diagram showing an additional imaging instruction information screen.

The display control unit 35 displays additional imaging instruction information on the display unit 3. FIG. 7 is a diagram showing an additional imaging instruction information screen displayed in the display unit 3. As shown in FIG. 7, an additional imaging instruction information display screen 40 includes an abnormal site type 41 (a tumor), an additional imaging type 42 (spot imaging), a compression plate type 43 (for spot imaging), and the specific image 44 representing the position of the abnormal site. In the specific image 44, a mark 44A is given to the position of the abnormal site.

Figure 8:
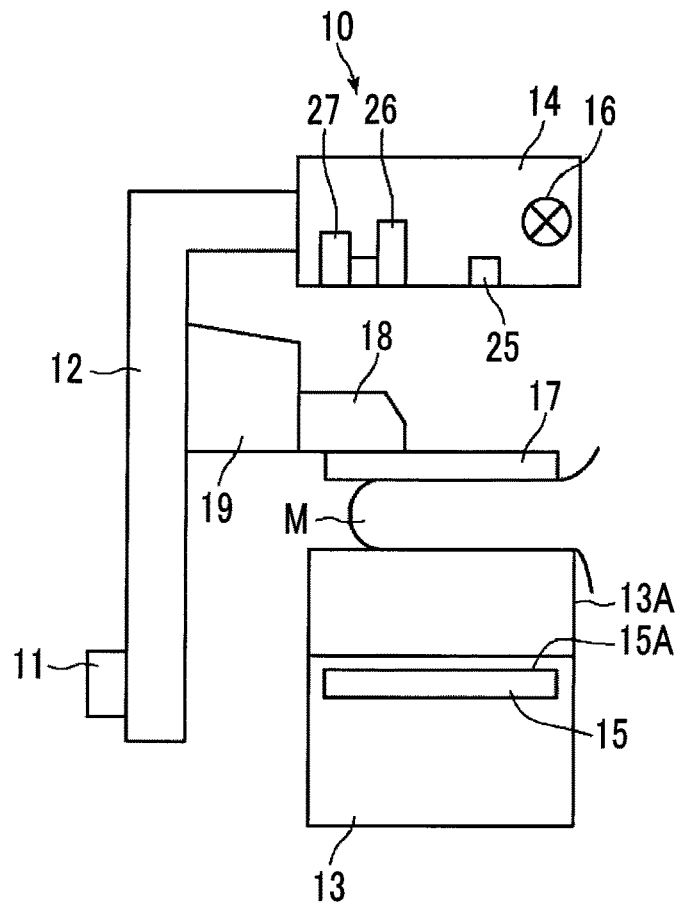
FIG. 8 is a diagram for explaining magnified imaging.

The operator performs additional imaging with respect to the breast M of the patient based on the additional imaging instruction information display screen 40 displayed in the display unit 3. Stated another way, the compression plate 17 is attached to the support unit 18 according to the compression plate type 43 and the breast M positioned so that the abnormal site of the breast M is within the imageable range, and as necessary, the height of the imaging table 13 is adjusted. In the case of performing magnified imaging, as shown in FIG. 8, an auxiliary imaging table 13A is installed on the imaging table 13, and the breast M is positioned on the auxiliary imaging table 13A to image the breast M. As a result, the distance between the breast M and the radiation detector 15 becomes larger than a case where only the imaging table 13 is used, and thus the radiation image of the enlarged breast M is detected by the radiation detector 15.

In a case of positioning, the camera 25 images the breast M positioned on the imaging table 13 or the auxiliary imaging table 13A (hereinafter, represented by the imaging table 13), and an optical image K1 representing the surface of the breast M is acquired as a prior image. The optical image K1 may be a moving image captured at a constant time interval, or may be a still image captured by imaging instruction from the input unit 4 after the breast M is positioned. The acquired optical image K1 is input to the determination unit 36 and the light source control unit 39.

Figure 9:
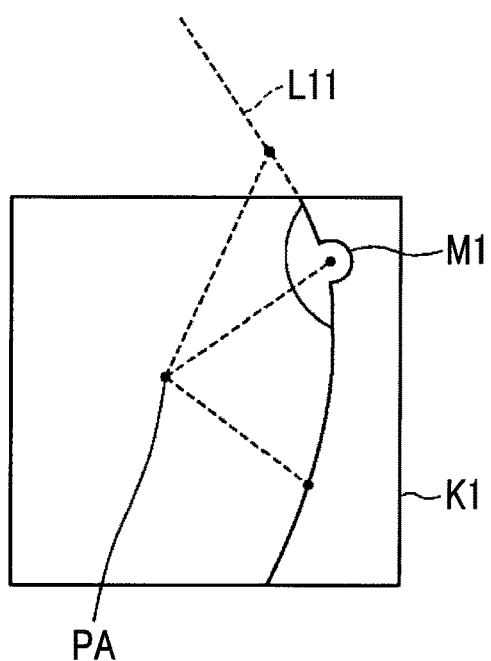
FIG. 9 is a diagram for explaining specifying of a position of the abnormal site in an optical image acquired during magnified imaging.

The determination unit 36 determines whether the position of the abnormal site is included in the imaging available region of additional imaging based on the positional information generated by the position specifying unit 33 and the optical image K1. For this purpose, the determination unit 36 specifies the position of the abnormal site in the optical image K1 based on the positional information of the abnormal site generated by the position specifying unit 33. In a case where additional imaging is not magnified imaging, the size of the breast M included in the optical image K1 is the same as the size of the breast image G1 generated by first imaging. Therefore, the position of the abnormal site in the breast M included in the optical image K1 can be immediately specified by using the positional information of the abnormal site. On the other hand, in a case where additional imaging is magnified imaging or spot imaging, the optical image K1 does not include the whole breast M as shown in FIG. 9. However, the optical image K1 includes the nipple and a part of the skin line. Therefore, as shown in FIG. 9, the determination unit 36 performs alignment between the skin line included in the optical image K1 and the skin line included in the breast image G1, draws a virtual skin line L11 in the plane including the optical image K1, and specifies the position PA of the abnormal site in the optical image K1 from the positional information of the abnormal site by using the virtual skin line L11, the nipple M1, and the skin line included in the optical image K1.

Figure 10:
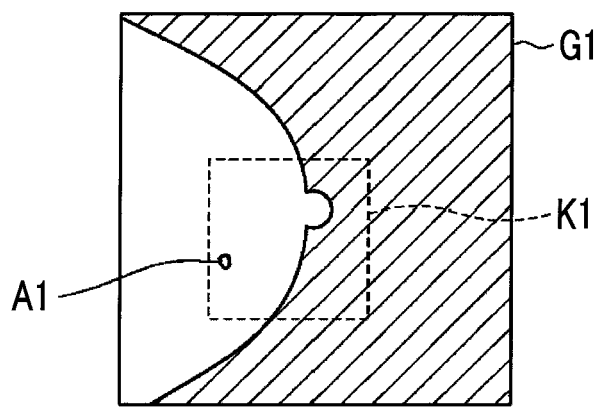
FIG. 10 is a diagram showing a state where the abnormal site is included in an optical image acquired during magnified imaging.

In a case where the breast M is positioned in the imaging available range of additional imaging, the optical image K1 indicated by a broken line in FIG. 10 includes the position of the abnormal site A1 detected in the breast image G1. In this case, the position of the abnormal site can be specified on the optical image K1 based on the positional information. On the other hand, in a case where the breast M is not positioned in the imaging available range of additional imaging, the optical image K1 indicated by a broken line in FIG. 11 does not include the position of the abnormal site A1 detected in the breast image G1. In this case, the position of the abnormal site cannot be specified on the optical image K1 even in a case of using the positional information.

Therefore, in a case where the determination unit 36 can specify the position of the abnormal site on the optical image K1 based on the positional information of the abnormal site, the position of the abnormal site is included in the optical image K1, so that the position of the abnormal site is determined to be included in the imaging available region of additional imaging. On the other hand, in a case where the position of the abnormal site on the optical image K1 cannot be specified even based on the positional information of the abnormal site, the position of the abnormal site is not included in the optical image K1, so that the position of the abnormal site is determined to be not included in the imaging available region of additional imaging.

The warning unit 37 issues a warning in a case where the determination unit 36 determines that the position of the abnormal site is not included in the imaging available region of additional imaging. As a warning, a message may be displayed on the display unit 3 indicating that the position of the abnormal site is not included in the imaging available region of additional imaging or may be output by voice, or the message may be a combination of display on the display unit 3 and voice output. In a case where the determination unit 36 determines that the position of the abnormal site is included in the imaging available region of additional imaging, the warning unit 37 displays a notice that the imaging is possible on the display unit 3. In this case, since additional imaging can be performed immediately, the warning unit 37 need only display a notice such as "Imaging is possible." on the display unit 3. As a result, the operator can instruct additional imaging from the input unit 4. The display control unit 35 may perform notice in a case where the position of the abnormal site is included in the imaging available region of additional imaging.

In a case where the position of the abnormal site is not included in the imaging available region of additional imaging, the positioning information output unit 38 outputs and displays positioning information for moving the breast M so that the abnormal site is included in the imaging available region to the display unit 3. The positioning information output unit 38 performs alignment between the breast image G1 and the optical image K1 in a case where the determination unit 36 determines that the position of the abnormal site is not included in the imaging available region of additional imaging. In this case, a contour image representing a skin line need only be generated from each of the breast image G1 and the optical image K1, and the contour images need only be aligned. As an alignment method, any known method such as morphing described in JP2001-120529A can be used.

Figure 11:
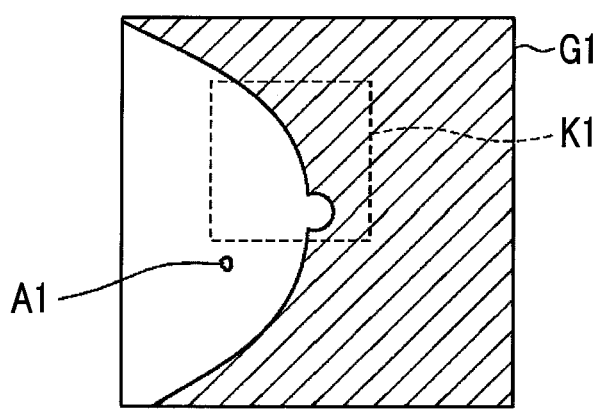
FIG. 11 is a diagram showing a state where the abnormal site is not included in the optical image acquired during magnified imaging.

In the case where the position of the abnormal site is not included in the imaging available region of additional imaging, the positional relationship between the breast image G1 and the optical image K1 is as shown in FIG. 11. The positioning information output unit 38 uses the positional relationship between the abnormal site A1 on the contour image of the breast image G1 and the contour image of the optical image K1 to determine the movement direction of the breast M so that the abnormal site A1 is positioned in the optical image K1. In the case shown in FIG. 11, the position of the abnormal site A1 is included in the imaging available region of additional imaging by moving the breast M to the upper side as viewed on the image, that is, to the left as viewed from the imaging table 13. Therefore, the positioning information output unit 38 generates, for example, a message "Please move the breast to the left." as positioning information, and outputs and displays the message on the display unit 3.

Figures 12, 13:
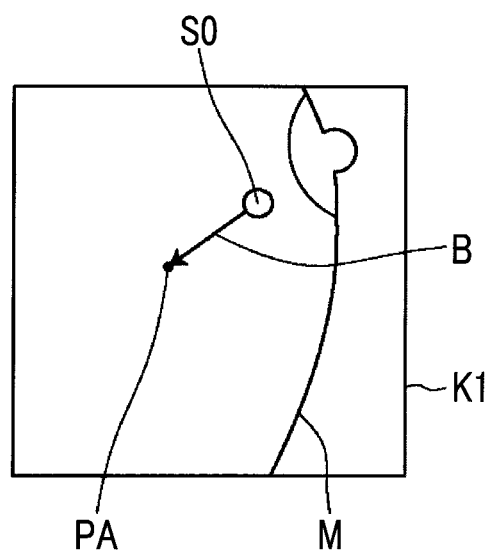
FIG. 12 is a diagram showing a warning display screen.
FIG. 13 is a diagram showing one image of the optical image acquired as a moving image.

Using the positional relationship between the position PA of the abnormal site on the breast image G1 and the optical image K1, a movement amount for positioning the position of the abnormal site A1 within the imaging available region of additional imaging may be derived, and the positioning information including the movement amount may be generated and output to the display unit 3. For example, a message "Please move the breast 5 cm to the left." may be generated as the positioning information and the message may be output and displayed to the display unit 3. The positioning information may be displayed in the display unit 3 including a warning by the warning unit 37. FIG. 12 shows a warning display screen showing a warning and the positioning information. As shown in FIG. 12, a message "An abnormal site is not included in the imaging available region. Please move the breast 5 cm to the left." is displayed in a warning display screen 45.

The light source control unit 39 controls the driving of the light source driving unit 27 based on the determination result by the determination unit 36. Stated another way, in a case where the determination unit 36 determines that the position of the abnormal site is included in the imaging available region of additional imaging, the light source control unit 39 drives the light source driving unit 27 so that the position of the abnormal site in the breast M positioned on the imaging table 13 is irradiated with spot light emitted from the spot light source 26. Specifically, the light source control unit 39 generates control information for controlling the spot light source 26 so that the abnormal site of the breast M on the imaging table 13 is irradiated with spot light emitted from the spot light source 26 and outputs the control information to the light source driving unit 27. As the spot light source 26, a laser light source, an LED light source, or the like can be used.

In a case where the direction of the spot light source 26 is controlled, the light source control unit 39 drives the camera 25 while emitting the spot light from the spot light source 26 toward the breast M, and acquires the optical image of the breast M irradiated with the spot light as the moving image at regular time intervals. FIG. 13 is a diagram showing one image of the optical image acquired as the moving image. As shown in FIG. 13, the optical image K1 includes an image of spot light S0 in addition to the breast M. Since the spot light S0 has higher brightness than the breast M, the light source control unit 39 detects the position of the pixel having higher brightness than a predetermined threshold in the optical image K1 as the position of the spot light S0. Then, the light source control unit 39 outputs a control signal, to the light source driving unit 27, for changing the direction of the spot light S0 emitted from the spot light source 26 to the direction indicated by the arrow B in FIG. 13 so that the detected spot light S0 is located at the position PA of the abnormal site. As a result, the light source driving unit 27 changes the direction of the spot light source 26. By repeating this processing until the spot light S0 matches the position PA of the abnormal site, the position of the abnormal site in the breast M is irradiated with the spot light S0. Thereby, the operator can recognize the position PA of the abnormal site in the breast M from the position of the spot light S0. In a case where the determination unit 36 determines that the position of the abnormal site is not included in the imaging available region of additional imaging, the light source control unit 39 may control the light source driving unit 27 so that the spot light is emitted outside the imaging available region of additional imaging.

Figure 14:
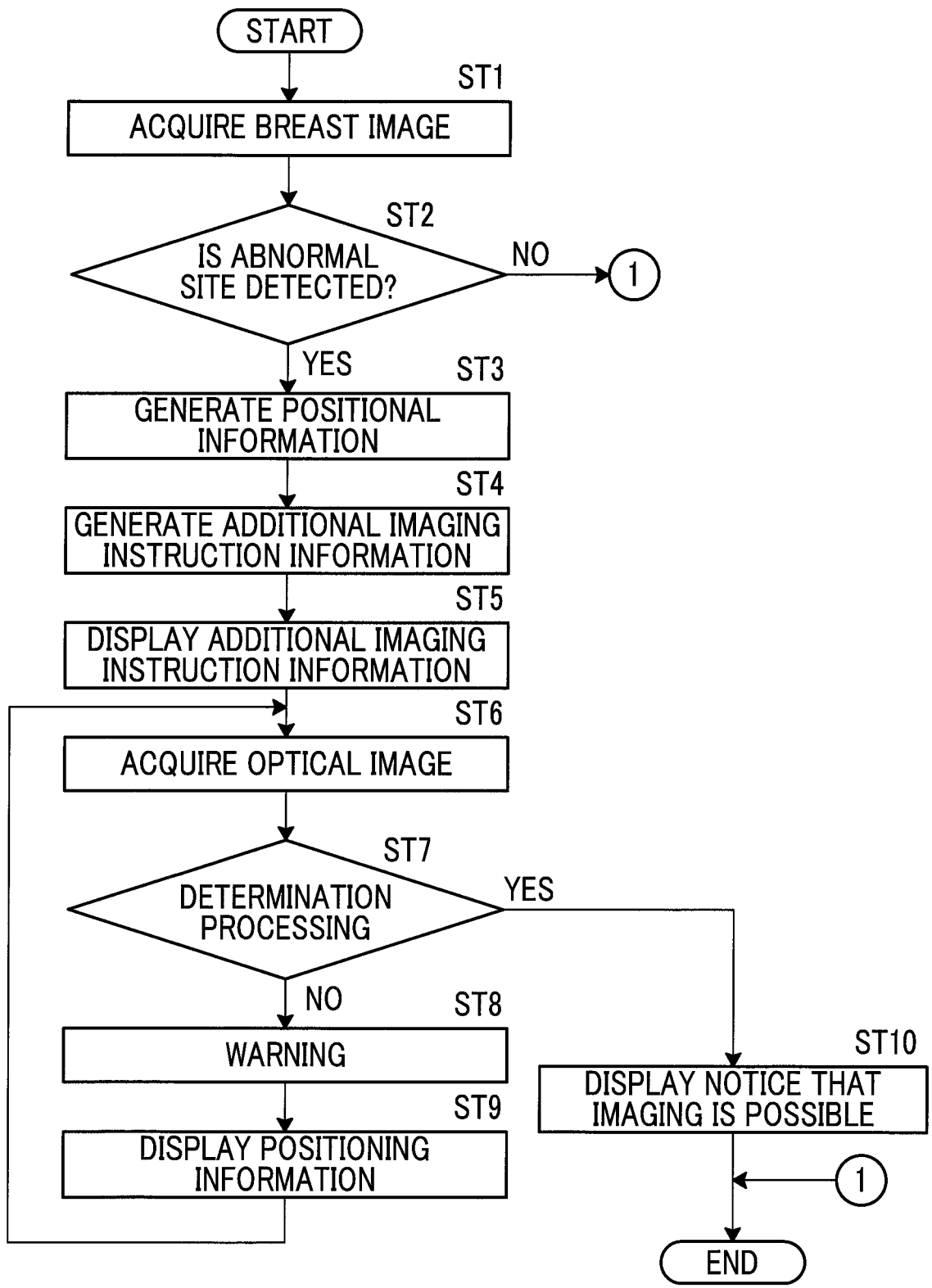
FIG. 14 is a flowchart showing a process performed in the present embodiment.

Next, the processing performed in the present embodiment will be described. FIG. 14 is a flowchart showing an imaging support process performed in the present embodiment. First, according to the instruction of the operator from the console 2, the image acquisition unit 31 drives the mammography apparatus 10 to acquire the breast image G1 (Step ST1). Next, the abnormal site detection unit 32 detects the abnormal site from the breast image G1 (Step ST2). In a case where the abnormal site is not detected (Step ST2: NO), the process ends. In a case where the abnormal site is detected (Step ST2: YES), the position specifying unit 33 generates the positional information for specifying the position of the abnormal site based on the feature point of the breast M included in the breast image G1 (Step ST3). Subsequently, the information generation unit 34 generates the additional imaging instruction information (Step ST4), and the display control unit 35 displays the additional imaging instruction information on the display unit 3 (Step ST5).

The operator performs operations such as positioning of the breast M for additional imaging based on the additional imaging instruction information displayed on the display unit 3. In a case where the operation is completed, the camera 25 images the breast M and acquires the optical image K1 based on the instruction from the console 2 by the operator (Step ST6). Next, the determination unit 36 determines whether the position of the abnormal site is included in the imaging available region of additional imaging based on the positional information and the optical image K1 (determination processing; Step ST7).

In a case of NO in Step ST7, the warning unit 37 issues a warning (Step ST8), and the positioning information output unit 38 outputs and displays the positioning information for positioning the abnormal site in the imaging available region on the display unit 3 (Step ST9), the processing returns to Step ST6, and the processing after Step ST6 is repeated. In a case of YES in Step ST7, the warning unit 37 displays a notice that imaging is possible on the display unit 3 (display a notice that imaging is possible: Step ST10), and the process ends. The operator performs the instruction for additional imaging from the console 2. Thereby, the image acquisition unit 31 drives the mammography apparatus 10 and performs additional imaging to acquire an additional breast image.

As described above, in the present embodiment, in a case where the abnormal site is detected in the breast image G1, the positional information for specifying the position of the abnormal site is generated based on the feature point of the breast M included in the breast image G1. Then, the additional imaging instruction information including information indicating the type of additional imaging based on the abnormal site and information indicating the position of the abnormal site based on the positional information is generated. Therefore, the operator can recognize the type of additional imaging and the position of the abnormal site with reference to the additional imaging instruction information. Accordingly, according to the present embodiment, it is possible to easily determine the necessity of additional imaging including a position to be additionally imaged.

In the present embodiment, the determination unit 36 determines whether the position of the abnormal site is included in the imaging available region of additional imaging based on the positional information and the optical image K1. Therefore, the operator can recognize whether the breast M is appropriately positioned during additional imaging with reference to the determination result.

In the present embodiment, a warning is issued in a case where the position of the abnormal site is not included in the imaging available region of additional imaging. Therefore, the operator can perform measures such as repositioning the breast M during additional imaging. In this case, the breast M can be positioned easily by referring to the positioning information output by the positioning information output unit 38.

Figure 15:
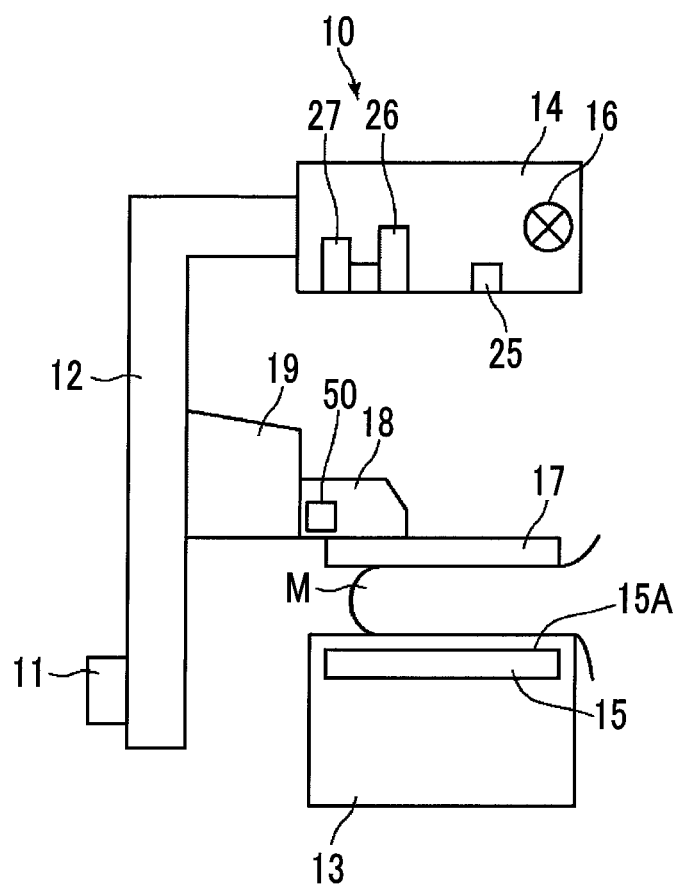
FIG. 15 is a diagram showing a mammography apparatus provided with a sensor that detects the type of the compression plate.

In the above embodiment, the mammography apparatus 10 may be provided with a sensor that detects the type of the compression plate 17 attached to the support unit 18. FIG. 15 is a diagram showing the mammography apparatus 10 provided with a sensor. As shown in FIG. 15, the sensor 50 is provided in the support unit 18 of the compression plate 17 of the mammography apparatus 10. In the present embodiment, it is assumed that the sensor 50 is an image sensor. Also, in a case where the compression plate 17 is attached to the support unit 18, it is assumed that a mark indicating the type of the compression plate 17 is given to the compression plate 17 at a position that can be imaged by the sensor 50. A mark image indicating the mark given to the compression plate 17 imaged by the sensor 50 is input to the determination unit 36.

Figure 16:
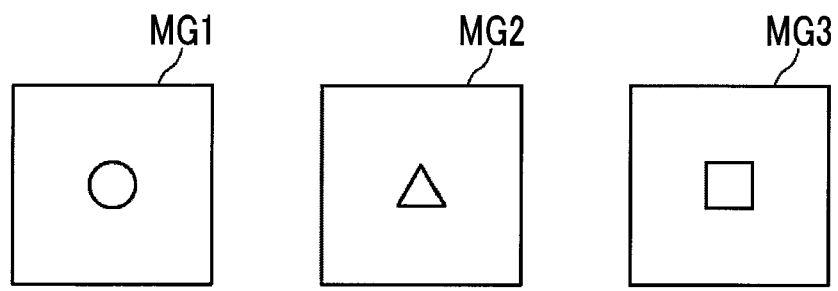
FIG. 16 is a diagram showing an example of a mark image.

FIG. 16 is a diagram showing an example of the mark image. Since the mark such as ○, △, and □ is given to the compression plate 17 depending on the type thereof, the sensor 50 images the mark given to the compression plate 17 and mark images MG1, MG2, and MG3 including ○, △, and □ shown in FIG. 16 are acquired. The determination unit 36 determines the type of the compression plate 17 attached to the support unit 18 based on the mark image output from the sensor 50. Then, the determination unit 36 compares the determined type of the compression plate 17 with the information on the type of the compression plate included in the additional imaging instruction information, and in a case where both do not match, information on that fact is output to the warning unit 37. The warning unit 37 displays a warning that the type of the compression plate 17 attached to the support unit 18 is different from the type of the compression plate included in the additional imaging instruction information on the display unit 3. For example, in a case where a small size compression plate for spot imaging is to be used, but a medium size compression plate for spot imaging is attached to the support unit 18, a message "The compression plate is different. Please use the small size compression plate for spot imaging." is displayed on the display unit 3. The warning unit 37 corresponds to the compression plate warning unit of the present disclosure. Thereby, the operator can easily recognize that the compression plate 17 attached to the support unit 18 is incorrect. Therefore, the operation which replaces the compression plate can be performed rapidly.

Figure 17:
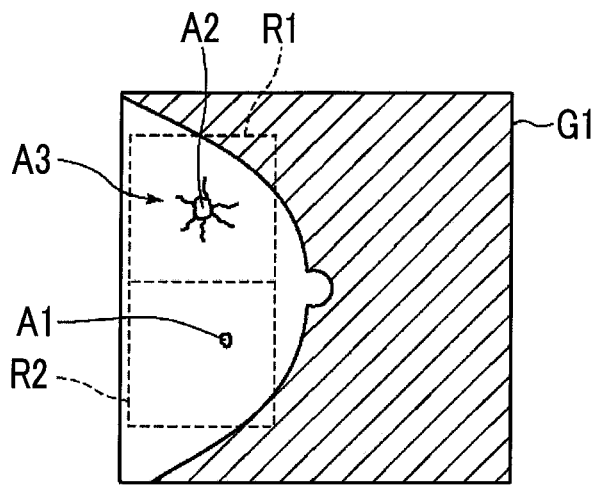
FIG. 17 is a diagram showing a breast image in which the abnormal site covers a wide range.

Meanwhile, there are cases where the existence range of the abnormal site is wide in the breast M, for example, there is a case where calcification is distributed over a wide area of the breast M or a tumor is large. In such a case, in the case of performing magnified imaging in additional imaging, it may not be possible to include all abnormal sites in the additional image acquired by additional imaging by one additional imaging. For example, as shown in FIG. 17, in a case where abnormal sites A1 to A3 are distributed over the entire breast M in the breast image G1, all the abnormal sites cannot be included in the imaging available regions R1 and R2 of one additional imaging. In such a case, as shown in FIG. 17, it is necessary to perform additional imaging of plural times (twice in FIG. 17).

Figure 18:
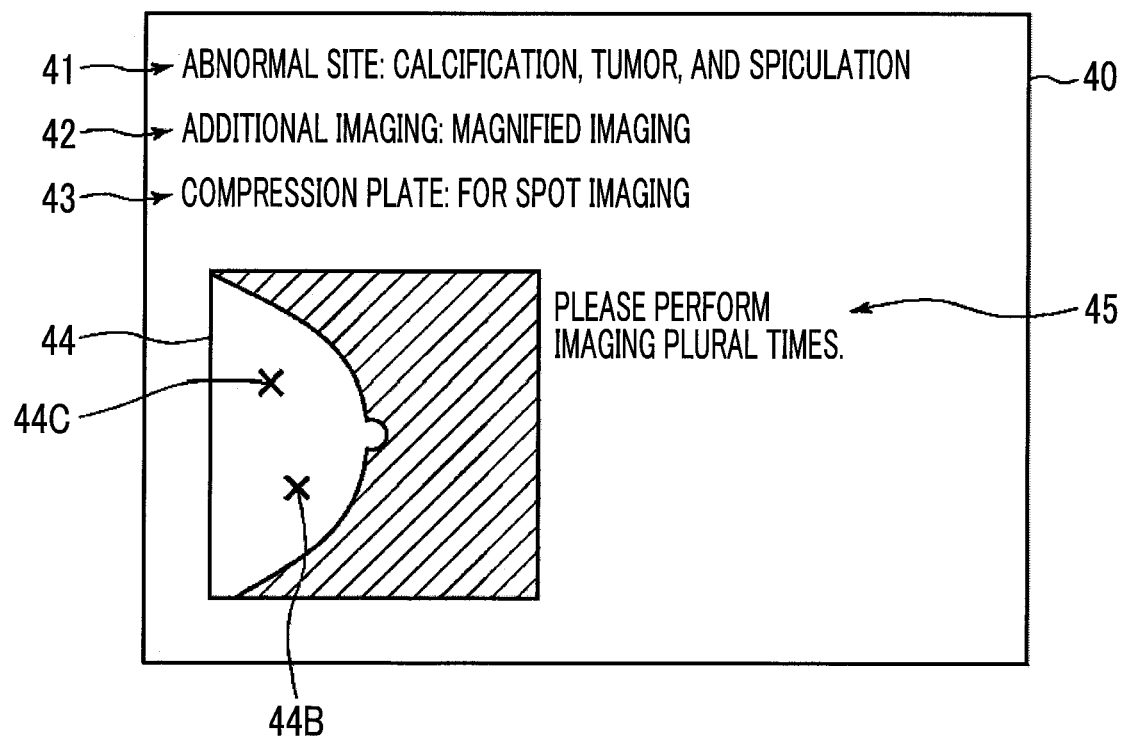
FIG. 18 is a diagram showing an additional imaging instruction information display screen.

Therefore, the information generation unit 34 compares the imaging available region of magnified imaging and the distribution of the abnormal site, and in a case where all the abnormal sites cannot be captured by one imaging, the information generation unit 34 generates the additional imaging instruction information for performing additional imaging of plural times. FIG. 18 is a diagram showing the additional imaging instruction information including the instruction to perform additional imaging of plural times displayed on the display unit 3. As shown in FIG. 18, an additional imaging instruction information display screen 40 includes the abnormal site type 41 (here, calcification, a tumor, and spiculation), the additional imaging type 42 (magnified imaging), the compression plate type 43 (for spot imaging), and the specific image 44 representing the position of the abnormal site, as in FIG. 7. In addition, a message 45 "Please perform imaging plural times." is included as an instruction to perform additional imaging of plural times. In the specific image 44, marks 44B and 44C indicating a plurality of abnormal sites are shown.

The operator performs additional imaging with respect to the breast M of the patient based on the additional imaging instruction information display screen 40 displayed in the display unit 3. Stated another way, the compression plate 17 is attached to the support unit 18 according to the compression plate type 43 and the breast M positioned so that the abnormal site of the breast M is within one imageable range, and as necessary, the height of the imaging table 13 is adjusted. In this case, every time one additional imaging is performed, the determination unit 36, the warning unit 37, and the positioning information output unit 38 performs the process in the same manner as in the above embodiment. Hereinafter, a process in a case of performing additional imaging of plural times will be described.

Figure 19:
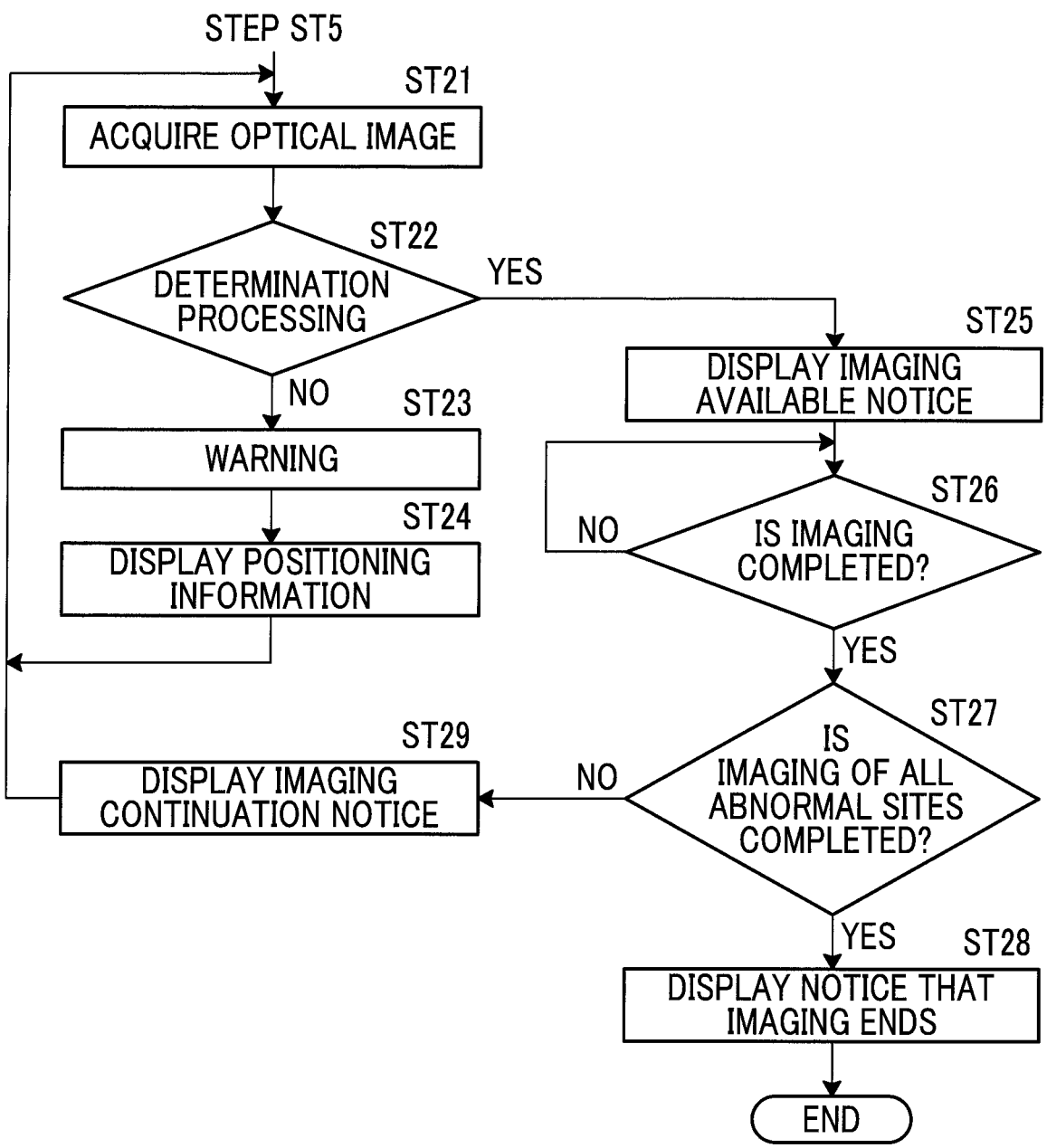
FIG. 19 is a flowchart showing a process in a case of performing additional imaging of plural times.

FIG. 19 is a flowchart showing the process in a case of performing additional imaging of plural times. In FIG. 19, the processing after Step ST5 in which the additional imaging instruction information is displayed in FIG. 14 will be described.

In a case where additional imaging instruction information including an instruction to perform additional imaging of plural times is displayed, the operator performs operations such as positioning of the breast M for additional imaging based on the additional imaging instruction information displayed on the display unit 3. In this case, since additional imaging of plural times is instructed, the operator first performs operation such as positioning for the first additional imaging. In a case where the operation is completed, the camera 25 images the breast M and acquires the optical image K1 based on the instruction from the console 2 by the operator (Step ST21). Next, the determination unit 36 determines whether the position of the abnormal site is included in the imaging available region of additional imaging based on the optical image K1 (determination processing; Step ST22).

In a case of NO in Step ST22, the warning unit 37 issues a warning (Step ST23), and the positioning information output unit 38 outputs and displays the positioning information for positioning the abnormal site in the imaging available region on the display unit 3 (Step ST24), the processing returns to Step ST21, and along with positioning of the breast M by the operator, the processing after Step ST21 is repeated. In a case of YES in Step ST22, the warning unit 37 displays a notice that imaging is possible on the display unit 3 (display of an imaging available notice: Step ST25). In a case where imaging is completed (Step ST26: YES), the determination unit 36 determines whether additional imaging is completed for all abnormal sites (Step ST27). The determination need only be performed by performing alignment between the optical image K1 and the breast image G1, and determining whether the abnormal site included in the breast image G1 is included in all the optical images captured so far.

In a case of YES in Step ST27, the warning unit 37 displays a notice that imaging ends on the display unit 3 (Step ST28), and the process ends. In a case of NO in Step ST27, the warning unit 37 displays an imaging continuation notice indicating that the next additional imaging is to be performed on the display unit 3 (display of an imaging continuation notice; Step ST29), and the processing returns to Step ST21.

In the above embodiment, the camera capable of acquiring the optical image K1 representing the surface of the breast M is used as the camera 25, but is not limited thereto. For example, a time of flight (TOF) camera that acquires a distance image representing the distance from the radiation source 16 to the surface of the breast M may be used.

In the above embodiment, the optical image K1 acquired by imaging the breast M by the camera 25 is used as the prior image, but is not limited thereto. Before the additional image is captured, in order to confirm the positioning of the breast M, pre-imaging for irradiating the breast M with a lower dose of radiation is performed than a case where the actual additional image is captured. Therefore, the image acquired by pre-imaging may be used as the prior image. In this case, the determination by the determination unit 36 need only be performed on the acquired pre-image for additional imaging by specifying an abnormal site in the same manner as described above. On the other hand, the abnormal site detection unit 32 detects the abnormal site from the pre-image, and using the detection result of the abnormal site with respect to the pre-image, the determination unit 36 may determine whether the position of the abnormal site is included in the imaging available region of additional imaging.

Figure 20:
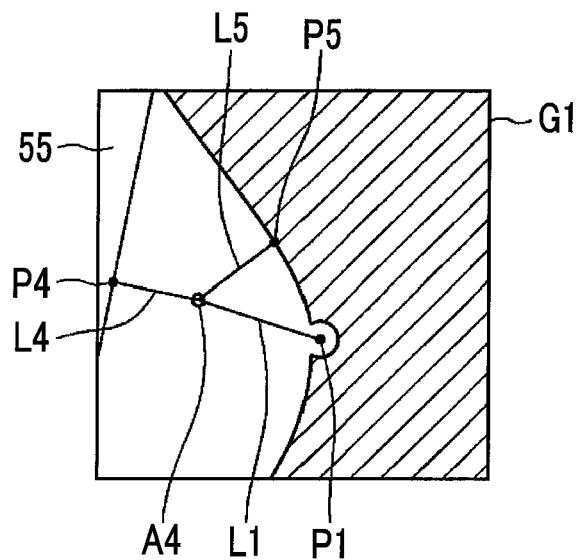
FIG. 20 is a diagram showing a breast image including a chest wall.

In the above embodiment, the nipple and the point on the skin line are used as the feature point of the breast M included in the breast image, but is not limited thereto. An intersection of blood vessels and an intersection of the outlines of the mammary gland included in the breast M in the breast image may be used as the feature point. Depending on the breast image capturing direction, the chest wall 55 may be included as shown in FIG. 20. In such a case, a point on the chest wall 55 where the distance L4 from the abnormal site A4 is minimum may be used as the feature point. In this case, the position specifying unit 33 need only specify the feature point P1 of the nipple position and the feature point P5 of the position of the skin line, and need only generate the distance L1 between the feature point P1 and the abnormal site A4 and the distance L5 between the feature point P5 and the abnormal site A4 in addition to the distance L4, as the positional information.

Figure 21:
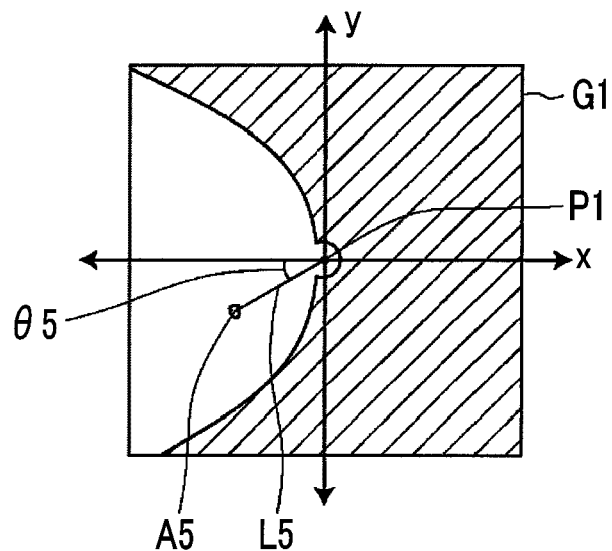
FIG. 21 is a diagram for explaining generation of positional information in a case where one feature point is specified.

In the above embodiment, the positional information for specifying the position of the abnormal site is generated using a plurality of feature points for the breast M included in the breast image, but is not limited thereto. For example, as shown in FIG. 21, the centroid position of the nipple is specified as one feature point P1, an x-y coordinate system with the feature point P1 as the origin is set, and the x coordinate of the abnormal site A5 and y coordinate in the set coordinate system may be generated as positional information. In this case, the position of the set origin may be included in the positional information, and a mark or the like may be given in a limited way to a case where the radiation image is displayed. Thereby, the operator can recognize where the origin for generating the positional information is set. Also, instead of the x-y coordinate system, a polar coordinate system centered on the feature point P1 may be set. The axis of the polar coordinate system passes through the feature point P1 and is in a direction perpendicular to the paper surface in FIG. 21. In this case, the distance L5 between the feature point P1 and the abnormal site A5 and an angle θ5 around the axis in the polar coordinate system need only be generated as positional information. Also, the one feature point to be specified is not limited to the centroid position of the nipple. A point on the skin line where the distance from the abnormal site A5 is the shortest or a point on the chest wall where the distance from the abnormal site A5 is the minimum may be used as one feature point.

In the embodiment, although the subject is the breast M, the subject is not limited to the breast, and any part of the human body such as the chest, abdomen, limbs, and head can be the subject.

The radiation in the embodiment is not particularly limited, and α rays or γ rays other than X-rays can be applied.

In the embodiment described above, for example, various processors shown below can be used as the hardware structures of processing units that execute various kinds of processing, such as the image acquisition unit 31, the abnormal site detection unit 32, the position specifying unit 33, the information generation unit 34, the display control unit 35, the determination unit 36, the warning unit 37, the positioning information output unit 38, and the light source control unit 39. The various processors include not only the CPU and a graphics processing unit (GPU), which is a general-purpose processor that executes software (program) and functions as various processing units, but also a programmable logic device (PLD) that is a processor whose circuit configuration can be changed after manufacture, such as a field programmable gate array (FPGA), and a dedicated electric circuit that is a processor having a circuit configuration that is designed for exclusive use in order to execute specific processing, such as an application specific integrated circuit (ASIC).

One processing unit may be configured by one of the various processors, or may be a combination of two or more processors of the same type or different types (for example, a combination of a plurality of FPGAs or a combination of a CPU and an FPGA). Alternatively, a plurality of processing units may be configured by one processor.

As an example of configuring a plurality of processing units by one processor, first, as represented by a computer, such as a client and a server, there is a form in which one processor is configured by a combination of one or more CPUs and software and this processor functions as a plurality of processing units. Second, as represented by a system on chip (SoC) or the like, there is a form of using a processor for realizing the function of the entire system including a plurality of processing units with one integrated circuit (IC) chip. Thus, various processing units are configured by one or more of the above-described various processors as a hardware structure.

More specifically, as the hardware structure of these various processors, it is possible to use an electrical circuit (circuitry) in which circuit elements such as semiconductor elements are combined.

What is claimed is:

1. An imaging support apparatus comprising:
at least one processor configured to:
detect an abnormal site included in a medical image acquired based on radiation transmitted through a subject;
generate positional information for specifying a position of the abnormal site based on a feature point of the subject included in the medical image in a case where the abnormal site is detected in the medical image; and
generate additional imaging instruction information, including information that indicates an imaging type based on the abnormal site and information that indicates the position of the abnormal site based on the positional information, for instructing at least one additional imaging.

2. The imaging support apparatus according to claim 1, wherein the at least one processor is further configured to:
make a determination as to whether the position of the abnormal site is included in a prior image acquired by prior imaging before instructing the at least one additional imaging based on the positional information and the prior image in a case where the at least one additional imaging is performed, and
based on a result of the determination, determine whether the position of the abnormal site is included in an imaging available region of the at least one additional imaging.

3. The imaging support apparatus according to claim 2, wherein in a case where the additional imaging instruction information is for instructing the at least one additional imaging of plural times, the at least one processor is further configured to determine whether the position of the abnormal site is included in each imaging available region of the at least one additional imaging of plural times.

4. The imaging support apparatus according to claim 2, wherein the prior image is an optical image representing a surface of the subject.

5. The imaging support apparatus according to claim 2, wherein the prior image is a pre-image acquired by irradiating the subject with the radiation before the at least one additional imaging.

6. The imaging support apparatus according to claim 2, wherein the at least one processor is further configured to issue a warning in a case where the position of the abnormal site is not included in the imaging available region of the at least one additional imaging.

7. The imaging support apparatus according to claim 2, wherein the at least one processor is further configured to output positioning information for positioning the abnormal site in the imaging available region in a case where the position of the abnormal site is not included in the imaging available region of the at least one additional imaging.

8. The imaging support apparatus according to claim 2, further comprising:
a light source that emits light toward the subject;
wherein the at least one processor is further configured to:
drive the light source so that the position of the abnormal site in a surface of the subject is irradiated with light emitted from the light source; and
control driving of the light source based on whether the position of the abnormal site is included in the imaging available region of the at least one additional imaging.

9. The imaging support apparatus according to claim 1, wherein the at least one processor is configured to detect an abnormal site included in a medical image acquired based on radiation transmitted through a breast.

10. The imaging support apparatus according to claim 9, wherein the at least one processor is further configured to generate the positional information for specifying the position of the abnormal site by detecting a nipple position of the breast and at least two positions on at least one of a skin line or a chest wall as the feature point of the subject.

11. The imaging support apparatus according to claim 9, wherein the at least one processor is further configured to generate the additional imaging instruction information including compression plate information indicating a type of a compression plate that compresses the breast.

12. The imaging support apparatus according to claim 11, wherein the at least one processor is further configured to issue a warning in a case where a compression plate used for the at least one additional imaging is different from the compression plate indicated by the compression plate information.

13. An imaging support method comprising:
   detecting an abnormal site included in a medical image acquired based on radiation transmitted through a subject;
   generating positional information for specifying a position of the abnormal site based on a feature point of the subject included in the medical image in a case where the abnormal site is detected in the medical image; and
   generating additional imaging instruction information, including information that indicates an imaging type based on the abnormal site and information that indicates the position of the abnormal site based on the positional information, for instructing at least one additional imaging.

14. A non-transitory computer-readable storage medium that stores an imaging support program that causes a computer to execute:
   a step of detecting an abnormal site included in a medical image acquired based on radiation transmitted through a subject;
   a step of generating positional information for specifying a position of the abnormal site based on a feature point of the subject included in the medical image in a case where the abnormal site is detected in the medical image; and
   a step of generating additional imaging instruction information, including information that indicates an imaging type based on the abnormal site and information that indicates the position of the abnormal site based on the positional information, for instructing at least one additional imaging.

* * * * *